United States Patent [19]

Tikka et al.

[11] Patent Number: 4,889,593

[45] Date of Patent: Dec. 26, 1989

[54] METHOD OF DETERMINING RAPIDLY THE CONCENTRATION OF THE TOTAL SULPHUR DIOXIDE AND THE LIGNOSULPHONATE PRESENT IN SULPHITE PULPING PROCESS LIQUORS

[75] Inventors: Panu Tikka; Nils E. Virkola, both of Helsinki, Finland

[73] Assignee: Oy Advanced Forest Automation Ab, Finland

[21] Appl. No.: 149,936

[22] Filed: Jan. 26, 1988

Related U.S. Application Data

[63] Continuation of Ser. No. 673,479, Nov. 20, 1984, abandoned.

[30] Foreign Application Priority Data

Dec. 30, 1983 [FI] Finland ............................ 834870

[51] Int. Cl.[4] .......................... D21C 3/04; D21C 3/06; D21C 3/22; D21C 7/12
[52] U.S. Cl. ........................................ 162/49; 162/61; 162/83; 210/662; 436/175
[58] Field of Search ................... 162/49, 238, 198, 50, 162/61, 62; 436/175, 161, 164, 129, 94; 210/662

[56] References Cited

FOREIGN PATENT DOCUMENTS 823574 10/1982 Finland.

OTHER PUBLICATIONS

Haglund et al. "Spectrophotometric Determination of the Dissolution of Lignin During Sulfite Cooking", *Tappi*, May 1964, vol. 47, No. 5 pp. 286-291.
Felicetta et al., "Spent Sulphite Liquor VII", *Tappi*, vol. 42, No. 6 Jun. 1959.

*Primary Examiner*—Steve Alvo
*Attorney, Agent, or Firm*—Scully, Scott, Murphy & Presser

[57] ABSTRACT

A method of rapid determination of the concentrations of the total sulphur dioxide and the lignosulphonate present in sulphite pulping process liquors. The lignosulphonates are separated from compounds which form the total sulphur dioxide by means of an ion exclusion column, whereby the filling material of the column consists of a cation exchange resin. The concentration measurements of the sulphur dioxide and the lignosulphonate are carried out from the liquor flow coming out from the separation column by means of UV-method at the wave length of 280 nm. The invention also relates to a method of controlling the sulphite pulping process by determining the total sulphite dioxide concentration in the pulping liquor.

3 Claims, 2 Drawing Sheets

METHOD OF DETERMINING RAPIDLY THE CONCENTRATION OF THE TOTAL SULPHUR DIOXIDE AND THE LIGNOSULPHONATE PRESENT IN SULPHITE PULPING PROCESS LIQUORS

This application is a continuation of application Ser. No. 673,479, filed 11/20/84, now abandoned.

BACKGROUND OF THE INVENTION

The invention relates to a method of rapid determination of the concentrations of the total sulphur dioxide and the lignosulphonates present in sulphite pulping process liquors.

The object of the invention was to provide a method for obtaining at short intervals measuring data on the concentration of the active "cooking" chemical for the sulphite cooking process, i.e. the compounds formed in the cooking liquor by the sulphur dioxide, and on the concentration of the lignosulphonate resulting from the pulping reactions for the control of the sulphite pulping process.

The invention is characterized in that the compounds which are formed in the liquor by the sulphur dioxide are separated from the lignosulphonates by means of an artificially effected ion exclusion phenomenon and that the concentration measurements are carried out from the liquor flow after the separation on the basis of the absorption of UV-radiation at a wave length of 280 nm. No mentions of a measuring method according to the present invention have been found in the literature.

In the digester house the cooking acid which is pumped into the sulphite pulping digester is usually analysed according to a certain standard by means of a laboratory titration method in order to determine the sulphur dioxide concentration. After the cooking has been started, no subsequent information will be obtained on the active cooking chemical. On account of variation in digester chip filling, wood density and moisture content as well as variation in the cooking process, the amount of lignin-dissolving sulphur dioxide compounds per amount of absolutely dry wood, however, varies from one charge to an other, which results in variation in the quality of the final product, which variation cannot be observed by means of the conventional measuring devices. Modern means for controlling cooking initial data, a mathematical model and a computer do not help solving these problems so that the need of devices following the actual cooking reactions and their proceeding is obvious. Attempts have been made to determine the concentration of the active cooking chemical during the cooking. In the lecture "On line cooking liquor analyzer—a means for effective control of sulfite digester", 1982 International Sulfite Pulping Conference, Toronto Oct. 20–22, 1982, TAPPI Proceedings, p. 285–292, Byland et al. disclose a method for controlling sulphite pulping, said method essentially comprising a sulphite cooking liquor analyzer operating according to the principle of titration. Said analyzer is realized in such a way that a titration method known per se has been automated, the concentration of the active cooking chemical being calculated at the equivalent point by means of a computer. Automating a titration method, however, requires several complicated and accurate feeding and dosing steps, which makes it liable to disturbances as well as expensive.

DETAILED DESCRIPTION OF THE INVENTION

Figure 1:
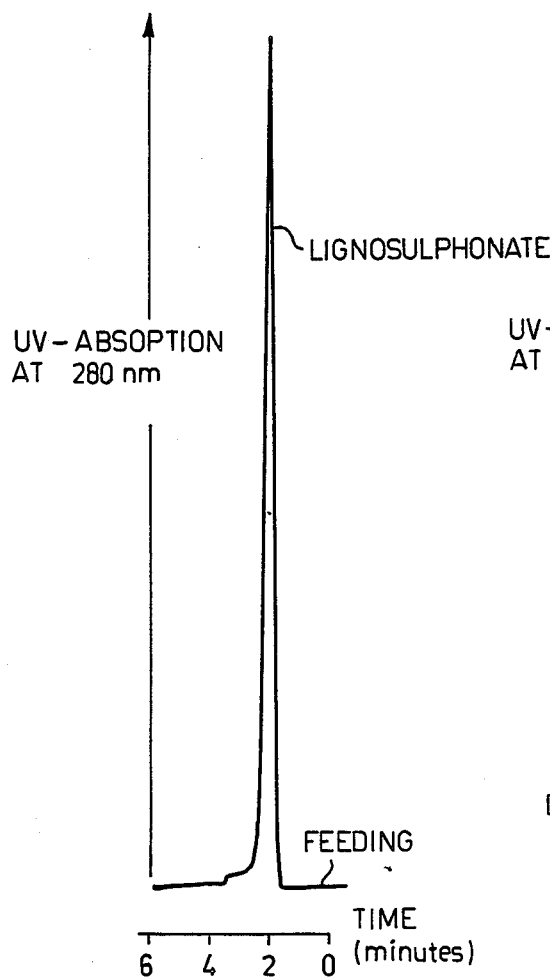
FIG. 1 is a graphic representation of the lignosulphonate content (separated) from a cooking process without pretreatment in accordance with the present invention (at 280 nm).

The present invention requires only one sample feed of an extremely small volume and easily automatizable by a loop injection valve.

The basic idea of the invention consists of pretreating a separation column based on the ion exclusion technique in such a way that the internal metal cation/proton balance of the column will be changed, thereby causing the separation resin environment to become acidic. The pretreatment of the column thus makes it possible for protons to remain in the column, whereby the internal pH of the column decreases. Once pretreated, column will not lose its acidity during the normal cooking control procedure, because the pH of the cooking liquor samples is as low as from 1 to 2, and there are enough of protons present in the sample to keep the column sufficiently acid. Besides, the total sulphur dioxide concentration of less acidic cooking liquors can be determined in such a way that a suitable amount of sufficiently acid sulphur dioxide solution is fed into the column between the samples, whereby the column is able to maintain its specific properties. In this way, the compounds present in the cooking liquor sample and formed in water solution by the sulphur dioxide are made to behave in a totally new way, i.e. they behave in an acid separation environment in the same way as non-ionized compounds. As a result the compounds forming the total sulphur dioxide are separated from the lignosulphonates and can be determined. The determination is based on the observation that the sulphur dioxide compounds dissolved in water have a by-maximum of the UV-radiation absorption spectrum at a wave length of 280 nm. It is highly advantageous to use said by-maximum in determining concentrations, because the by-maximum of the UV-spectrum of the lignosulphonate present in the cooking liquor is also at said wave length. Concentration data on both the lignin dissolved from wood and on the active chemical will thus be provided extremely practically and specifically. Said UV-measuring also totally avoids problems caused by organic compounds coming to the measuring process together with the total sulphur dioxide due to the conventional ion exclusion separation, because these compounds do not absorb UV-radiation at 280 nm and, accordingly, do not affect the measuring of the total sulphur dioxide.

In the present method, a rapid separation column according to Finnish Patent Application 823,574 developed for the determination of the lignosulphonates, monosaccharides and organic acids present in sulphite pulping process liquors is used. Said column is pretreated by waste liquor samples treated with sulphur dioxide by feeding said samples into the column as long as the data curves obtained by the measuring equipment show proper operation of the sulphur dioxide analysis. With respect to the control of the pulping process, it is especially advantageous to use a pretreated separation column in combination with the measuring equipment disclosed in Patent Application 823,574, thereby obtaining measuring data on dissolved lignin, dissolved non-lignin material (cellulose and hemi-cellulose) and the active cooking chemical in the cooking liquor.

The following examples illustrate the invention.

EXAMPLE 1

Pretreatment of an ion exclusion separation column for the determination of the total sulphur dioxide concentration in a sulphite cooking liquor.

At the end of a cooking there was fed into an ion exclusion column, 30 $\mu$l of a calcium sulphite cooking liquor to which sulphur dioxide gas had been led over a period of 10 minutes. The ion exclusion column, the diameter and length of which were 10 mm and 21 cm respectively and which had a "BioRad AG50Wx4" 200–400 mesh cation exchange resin in $Ca^{2+}$-form as ion exclusion material, was being eluted by means of clean gasless water 3.6 ml per minute at a temperature of 60° C. Said feeding of 30 $\mu$l was repeated 15 times successively, whereafter the total sulphur dioxide was easily distinguishable and could be separated from the lignosulphonates and thereby made quantitatively useful.

A "Knauer UV-Filterphotometer" and a flow-through cuvette of 0.4 mm were used in the UV-spectrophotometric determination, the measuring wave length being 280 nm. The data curves obtained by the measurements are shown in FIGS. 1 and 2.

Figure 2:
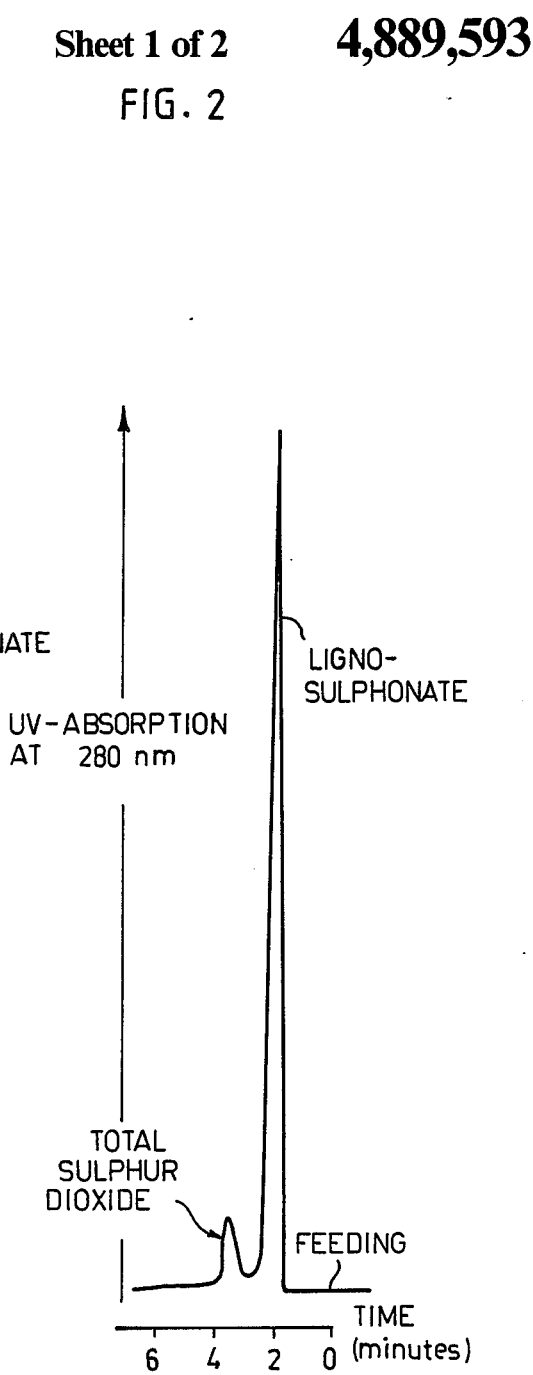
FIG. 2 is a graphic representation of the sulphur dioxide content measured in accordance with the process of the present invention (at 280 nm).

FIG. 1 illustrates a separation carried out by a conventional rapid separation column intended for determining of the organic compounds in a sulphite cooking liquor. Only one peak consisting of lignosulphonate is to be seen and, besides, an indefinite tail. The sulphur dioxide cannot be determined. FIG. 2 illustrates a situation where the column has been pretreated 15 times with a waste liquor sample containing sulphur dioxide according to the above example. It is noted that the sulphur dioxide compounds contained in the sample form their own distinctive peak after the lignosulphonates. The total sulphur concentration of the sample can be easily and rapidly determined.

EXAMPLE 2

Use of the sulphur dioxide measuring device according to the invention for measuring the total sulphur dioxide concentrations in sulphite cookings.

Figure 3:
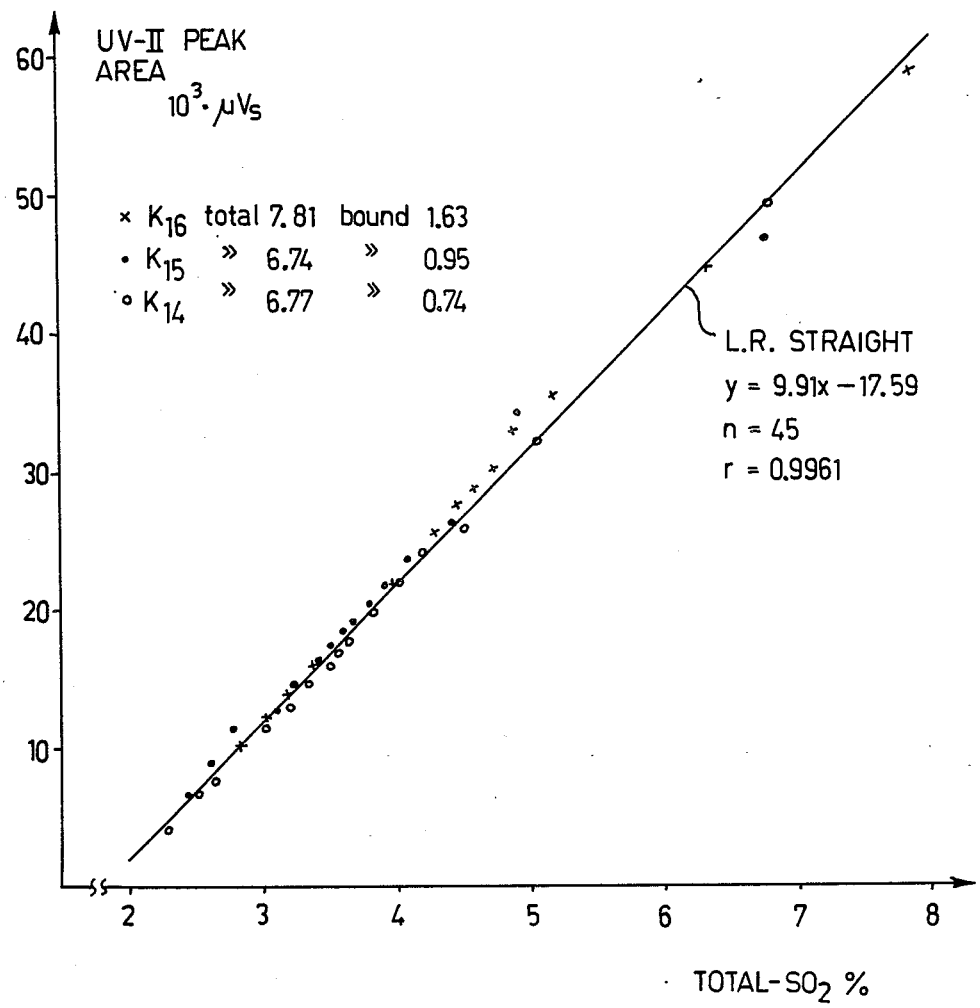
FIG. 3 is a graphic representation of the total sulphur dioxide content as measured in accordance with the process of the present invention.

Three acid calcium sulphite cooking charges were cooked of fir chips by means of a forced circulation digester of 20 liters. The ratio liquor/wood in the charges was 4.5:1, the cooking temperature 135° C. and the pressure time 212 minutes. The composition of the cooking acid was varied within the range of 6.8 to 7.8% total sulphur dioxide and from 0.59 to 1.63% bound sulphur dioxide. Samples were taken out of the digester every 20 minutes for the automated measuring device according to the present invention, and hand samples into bottles, which were immediately titrated by means of the standard procedure. The results were presented in the form of a curve, where the total sulphur dioxide concentration determined by the measuring device as the area of the sulphur dioxide peak was shown as a function of the concentration determined by titration. The curve obtained is shown in FIG. 3. It is noted that the results are positioned on the same straight line regardless of that the composition of the cooking acid has been altered within wide limits. The curve can thus be used as a calibration curve, by means of which the total sulphur dioxide concentration in the cooking acids as well as in the cooking liquors during the pulping process can be determined.

We claim:

1. A method for controlling a sulphite pulping process wherein the pulping liquor contains compounds of sulphur dioxide and lignosulphonate comprising:
    (a) pretreating an ion exclusion column with sulphur dioxide thereby acidifying said column;
    (b) separating the compounds forming the total sulphur dioxide concentration from the compounds forming the lignosulphonate concentration of said pulping liquor by passing said liquor through said pretreated column;
    (c) spectrophotometrically determining the concentration of said sulphur dioxide by measuring the ultraviolet light absorbance at a wavelength of 280 mm, of the liquid effluent from said column pretreated with said sulphur dioxide;
    (d) regulating the pulping temperature and time in response to said determined sulphur dioxide concentration; and
    (e) matintaining the column acidity throughout the controlling of the said pulping.

2. A method according to claim 1, wherein the concentration of sulphur dioxide is determined periodically at intervals of 20 minutes.

3. A method according to claim 1, wherein said ion exclusion column contains a cationic exchange resin, the internal pH of which is maintained at a level sufficient to maintain said acidic conditions for separating the compounds forming the sulfur dioxide concentration from the compounds forming the lignosulfonate concentration.

* * * * *